US009474479B2

(12) United States Patent
Pusey et al.

(10) Patent No.: US 9,474,479 B2
(45) Date of Patent: Oct. 25, 2016

(54) UNI-DIRECTIONAL DRIVE MECHANISM FOR LANCING DEVICE

(71) Applicant: FACET TECHNOLOGIES, LLC, Kennesaw, GA (US)

(72) Inventors: Lauren R. Pusey, Woodstock, GA (US); Carmine L. Cuda, Springfield, VA (US)

(73) Assignee: FACET TECHNOLOGIES, LLC, Atlanta, GA (US)

( * ) Notice: Subject to any disclaimer, the term of this patent is extended or adjusted under 35 U.S.C. 154(b) by 109 days.

(21) Appl. No.: 13/920,660

(22) Filed: Jun. 18, 2013

(65) Prior Publication Data
US 2013/0338537 A1 Dec. 19, 2013

Related U.S. Application Data

(60) Provisional application No. 61/660,970, filed on Jun. 18, 2012.

(51) Int. Cl.
*A61B 5/151* (2006.01)
*A61B 5/15* (2006.01)

(52) U.S. Cl.
CPC .......... *A61B 5/15117* (2013.01); *A61B 5/1411* (2013.01); *A61B 5/1519* (2013.01); *A61B 5/150022* (2013.01); *A61B 5/15113* (2013.01); *A61B 5/15128* (2013.01); *A61B 5/150183* (2013.01); *A61B 5/15194* (2013.01); *A61B 5/150412* (2013.01); *A61B 5/150503* (2013.01)

(58) Field of Classification Search
CPC ............ A61B 5/1411; A61B 5/15117; A61B 5/1513; A61B 5/15132; A61B 5/15128; A61B 5/1519; A61B 5/15126

USPC .......... 600/583; 606/172, 181, 182; 604/117
See application file for complete search history.

(56) References Cited

U.S. PATENT DOCUMENTS

| 4,539,988 A | 9/1985 | Shirley et al. |
| 4,643,189 A | 2/1987 | Mintz |
| 5,035,704 A | 7/1991 | Lambert et al. |
| 5,133,730 A | 7/1992 | Biro et al. |
| 5,212,879 A | 5/1993 | Biro et al. |
| 5,314,441 A | 5/1994 | Cusack et al. |

(Continued)

FOREIGN PATENT DOCUMENTS

| DE | 102008037082 A1 | 12/2009 |
| EP | 0458451 A1 | 11/1991 |

(Continued)

OTHER PUBLICATIONS

International Search Report & Written Opinion for PCT/US2013/046317; Oct. 7, 2013; 13 pgs.

*Primary Examiner* — Devin Henson
*Assistant Examiner* — David J McCrosky
(74) *Attorney, Agent, or Firm* — Gardner Groff Greenwald & Villanueva, PC

(57) ABSTRACT

A lancing device having a drive mechanism whereby uni-directional motion of the drive mechanism drives a lancet along an advancing portion and a retraction portion of a lancing stroke. A rotationally mounted crank member or a translationally mounted shuttle of the drive mechanism operate upon an associated linkage and/or a cam path portion of the lancet carrier to drive the carrier along the lancing stroke. Spring biased members optionally drive the mechanism and/or limit its extent of travel.

7 Claims, 14 Drawing Sheets

(56) References Cited

U.S. PATENT DOCUMENTS

| | | |
|---|---|---|
| 5,476,474 A | 12/1995 | Davis et al. |
| 5,527,334 A | 6/1996 | Kanner et al. |
| 5,545,174 A | 8/1996 | Schenk et al. |
| 5,628,765 A | 5/1997 | Morita |
| 5,645,555 A | 7/1997 | Davis et al. |
| 5,772,677 A | 6/1998 | Mawhirt et al. |
| 5,782,852 A | 7/1998 | Foggia et al. |
| 5,951,582 A | 9/1999 | Thorne et al. |
| 6,010,519 A | 1/2000 | Mawhirt et al. |
| 6,221,089 B1 | 4/2001 | Mawhirt |
| 6,409,740 B1 | 6/2002 | Kuhr et al. |
| 6,858,015 B2 | 2/2005 | List |
| 6,929,649 B2 | 8/2005 | Pugh |
| 7,144,404 B2 | 12/2006 | Whitson et al. |
| 7,160,313 B2 | 1/2007 | Galloway et al. |
| 7,316,698 B1 | 1/2008 | Galloway et al. |
| 7,452,365 B2 | 11/2008 | Galloway et al. |
| 7,691,117 B2 | 4/2010 | Whitson et al. |
| 7,704,265 B2 | 4/2010 | Schraga |
| 7,763,042 B2 | 7/2010 | Iio et al. |
| 7,879,058 B2 | 2/2011 | Ikeda |
| 8,034,068 B2 | 10/2011 | Koeppel et al. |
| 8,105,347 B2 | 1/2012 | Schraga |
| 8,512,367 B2 | 8/2013 | Robbins et al. |
| 2005/0131441 A1* | 6/2005 | Iio et al. ................ 606/182 |
| 2005/0256534 A1 | 11/2005 | Alden et al. |
| 2005/0283177 A1 | 12/2005 | Chen |
| 2006/0259057 A1 | 11/2006 | Kim et al. |
| 2008/0097502 A1 | 4/2008 | Winters-Hilt et al. |
| 2008/0262388 A1* | 10/2008 | List et al. ............... 600/583 |
| 2009/0054812 A1 | 2/2009 | Mace |
| 2011/0144683 A1* | 6/2011 | Butz ................ A61B 5/1411 606/182 |

FOREIGN PATENT DOCUMENTS

| | | |
|---|---|---|
| EP | 1090584 A2 | 4/2001 |
| EP | 1779781 A2 | 5/2007 |
| EP | 1797822 A1 | 6/2007 |
| EP | 1847219 A1 | 10/2007 |
| EP | 2438946 A1 | 4/2012 |
| JP | 6442010 U | 3/1989 |
| JP | 2000245715 A | 9/2000 |
| WO | 9604857 A1 | 2/1996 |

\* cited by examiner

UNI-DIRECTIONAL DRIVE MECHANISM FOR LANCING DEVICE

CROSS-REFERENCE TO RELATED APPLICATION

This application claims the priority benefit of U.S. Provisional Patent Application Ser. No. 61/660,970 filed Jun. 18, 2012, the entirety of which is hereby incorporated herein by reference for all purposes.

TECHNICAL FIELD

The present invention relates generally to the field of medical devices, and more particularly to a lancing device for blood sampling and testing that provides minimal user discomfort and user pain, actual and/or perceived, and incorporated drive mechanisms for propelling a lancet along a lancing stroke without oscillation due to spring balancing.

BACKGROUND

Lancing devices are utilized for penetrating the skin of a human or animal subject at a lancing site to obtain a sample of blood or other body fluid for medical testing, as in blood-typing or blood-glucose testing. Known lancing devices commonly include a housing containing a drive mechanism, a charging mechanism for energizing the spring or other drive means of the drive mechanism, and a release mechanism for releasing the drive mechanism upon actuation. A lancet is typically propelled by the drive mechanism from a retracted position within the housing to an extended position wherein a sharp tip portion of the lancet projects from the housing to prick the subject's skin at a desired lancing site. A depth-control mechanism can optionally be provided for adjusting the penetration depth of the lancet.

Many known lancing devices use drive mechanisms that rely on a balance between two linear (compression) springs for driving and retracting the lancet, resulting in the possibility of the lancet needle piercing the subject multiple times. Additionally, many known lancing devices use depth-control mechanisms for controlling the depth of puncture of the lancet needle by stopping the forward motion of the lancet, resulting in an impact that can be undesirably felt and/or perceived by the subject. Some known lancing devices may allow oscillation of the lancet in response to the balance of forces imparted by the drive and return springs, creating a potential for pricking the skin of the subject multiple times, which can unnecessarily result in pain to the subject. Additionally, some known lancing devices have depth-control mechanisms for stopping the forward motion of the lancet carrier by contact with a stop surface, which can result in impact, vibration or sound perceived by the user, and potentially increasing the perception of pain from lancing.

There is an ongoing need for improvements to lancing devices and drive mechanisms for lancing devices to increase convenience and compliance with a prescribed testing regimen, and to reduce the perception of pain by testing subjects. It is to the provision of improved lancing devices and drive mechanisms for lancing devices meeting these and other needs that the present invention is primarily directed.

SUMMARY

In example embodiments, the present invention provides improved lancing devices and improved drive mechanisms for lancing devices. In example forms, movement of a drive mechanism along a continuous uni-directional drive path imparts a back-and-forth movement of a lancet or lancet carrier along a defined lancing stroke, eliminating the potential for oscillation and multiple sticks by the lancet. Resilient biasing members at opposed sides of the drive path energize the drive mechanism and limit traverse of the lancet or lancet carrier without impact upon a hard stop member.

In one aspect, the present invention relates to a lancing device for propelling a lancet along a lancing stroke. The lancing device has a housing having a proximal end, a distal end and a longitudinal axis, and a drive mechanism movably mounted within the housing. The drive mechanism has a lancet carrier translationally mounted for axial movement within the housing, a link having a first end coupled to the lancet carrier and a second end extending generally opposite thereto, and a drive crank mechanism movably mounted within the housing. The drive crank mechanism has a rotatable crank member coupled to the second end of the link and at least two biasing members for energizing the drive crank mechanism and limiting a degree of rotation of the crank member. Preferably, one continuous rotational movement of the rotatable crank member propels the lancet carrier along the lancing stroke.

In another aspect, the invention relates to a drive mechanism for a lancing device. The drive mechanism includes a lancet carrier translationally mounted to a portion of the lancing device for movement along a first axis, and a drive crank mechanism rotationally mounted to a portion of the lancing device. The drive crank mechanism has a crank member mounted for rotation about a second axis, and at least two biasing members for actuating the drive mechanism and limiting a degree of rotation of the crank member. A link couples the lancet carrier to the crank member whereby a continuous rotational movement of the crank member drives the lancet carrier along the first axis in both a first or advancing direction and a second or retracting direction.

In still another aspect, the invention relates to a drive mechanism for a lancing device. The drive mechanism includes a lancet carrier and a drive crank mechanism. The lancet carrier includes a proximal end for receiving a lancet and a distal end defining a cam path. The lancet carrier is mounted to a portion of the lancing device for translational movement along a first axis. The drive crank mechanism includes a crank member rotatable about a second axis and first and second biasing members for rotationally driving the crank member and constraining its rotation between first and second angular rotational positions. A pin extends from the crank member and slides along the cam path of the lancet carrier. Preferably, one continuous rotational motion of the crank member about the second axis and within a degree of rotation between the first and second positions, moving the pin along the cam path, and moving the lancet carrier through a lancing stroke in the first axis in both a first direction and a second direction.

In yet another aspect, the present invention relates to a drive mechanism for a lancing device. The drive mechanism includes a lancet carrier and a drive shuttle mechanism. The lancet carrier includes a proximal end for receiving a lancet and a distal end defining a cam path, and translationally mounts to a portion of the lancing device for movement along a first axis. The drive shuttle mechanism movably mounts to another portion of the lancing device. The drive shuttle mechanism includes a shuttle member movably mounted within an elongated guide for translational movement along a second axis extending generally transverse to the first axis, a first biasing member and a second biasing member coupled to the shuttle alongside the cam path for driving translational movement of the shuttle member and limiting the movement of the shuttle member within a defined range. A pin extending from the shuttle member is movably mounted to traverse the cam path of the lancet carrier to drive the lancet carrier along the first axis in response to movement of the shuttle member along the second axis. Preferably, one continuous motion of the shuttle member along the second axis within the defined range of movement moves the pin along the cam path, moving the lancet carrier along the first axis.

In still another aspect, the present invention relates to a method of propelling a lancet along a lancing stroke. The method preferably includes translationally mounting a lancet carrier within a portion of the lancing device, movably mounting a drive mechanism within a portion of the lancing device, coupling a portion of the lancet carrier to a portion of the drive mechanism, moving the drive mechanism in a single-direction to actuate the lancet carrier, and moving the lancet carrier in a first direction and in a second direction responsive to the single-direction motion of the drive mechanism.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
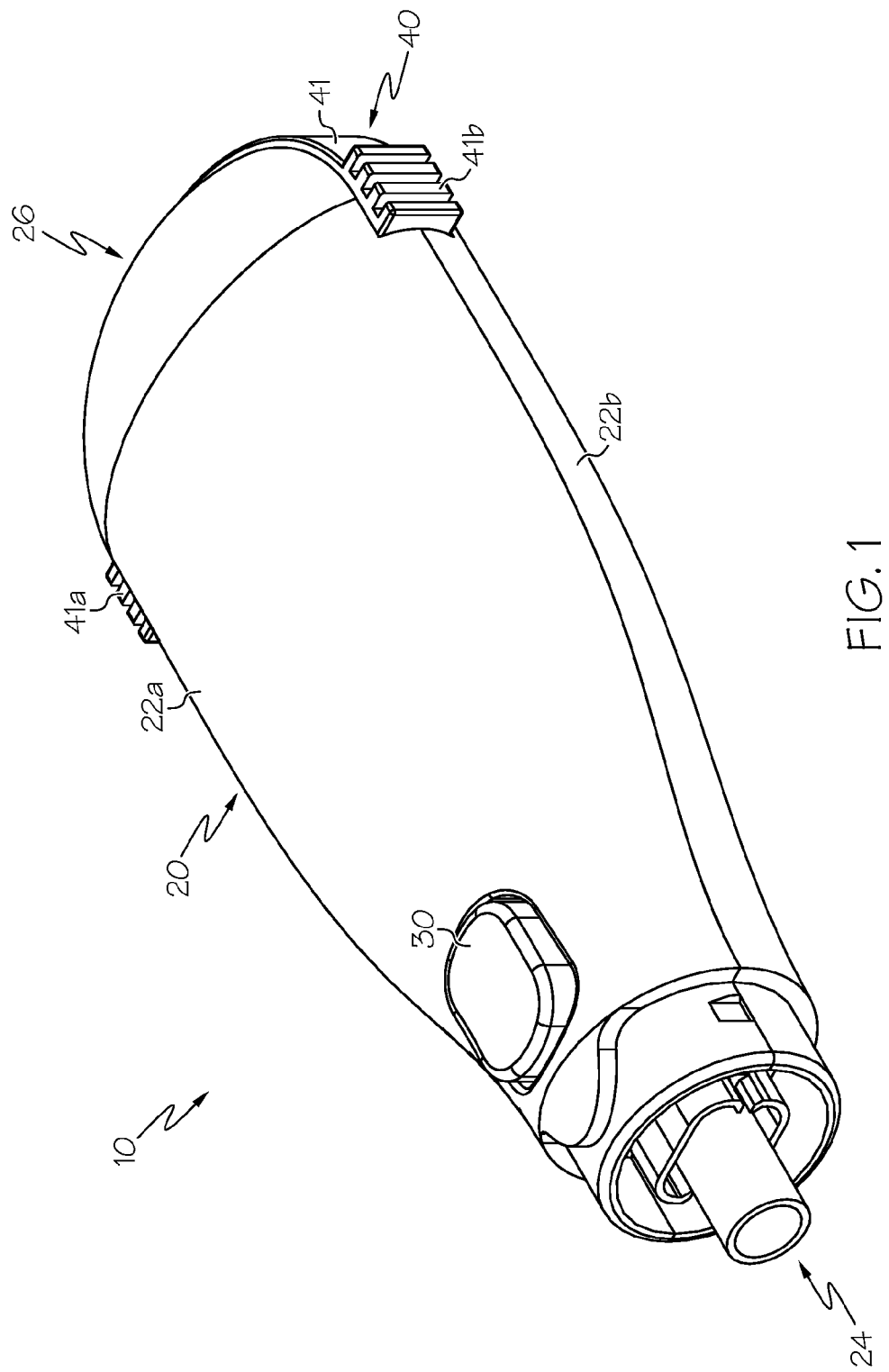
FIG. 1 is a front perspective view of a lancing device according to an example embodiment of the present invention.
Figure 2:
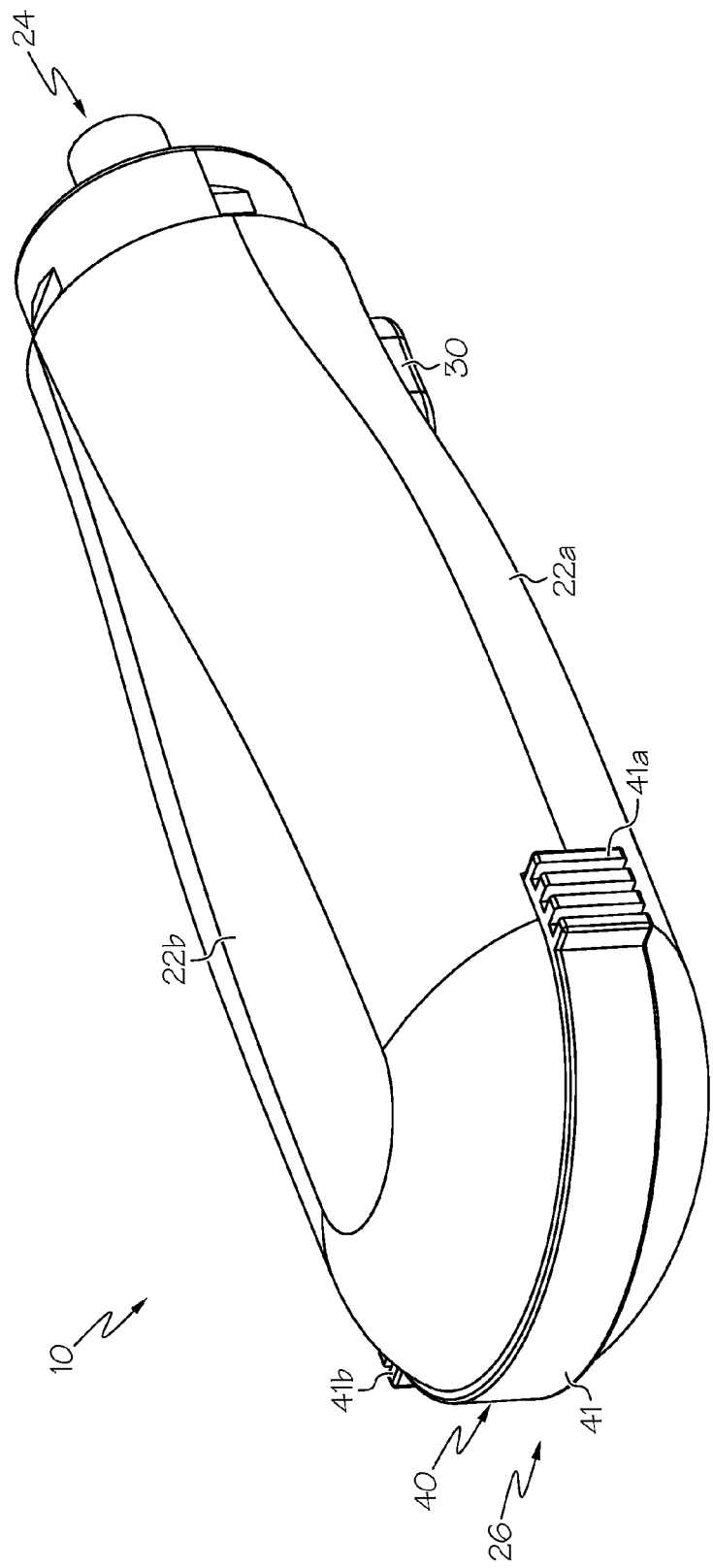
FIG. 2 is a rear perspective view of the lancing device of FIG. 1.
Figure 3:
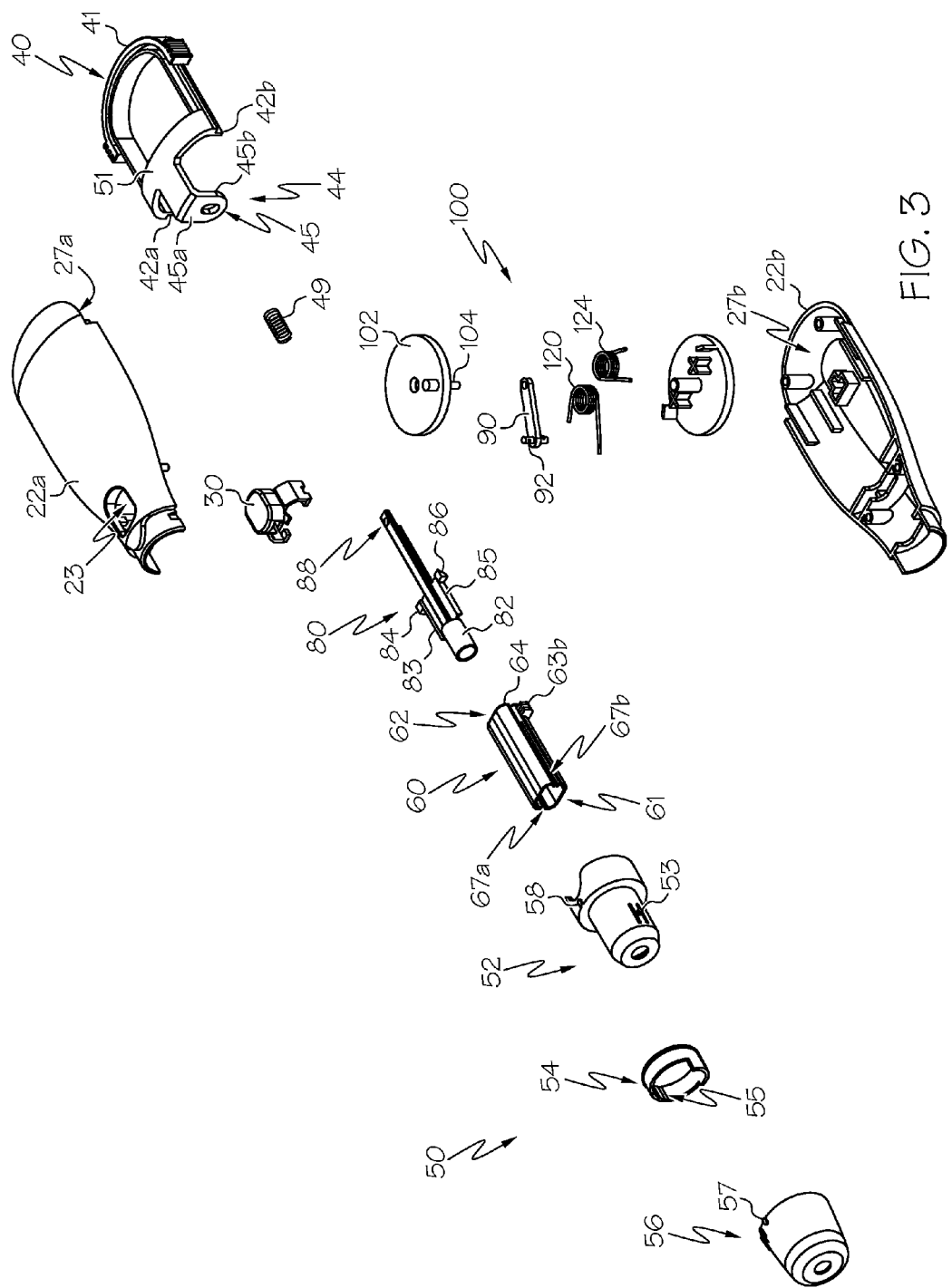
FIG. 3 is an assembly view of the lancing device of FIG. 1.

With reference now to the drawing figures, wherein like reference numbers represent corresponding parts throughout the several views, FIGS. 1-12 show various aspects and features of a lancing device 10 according to example forms of the present invention. FIGS. 1-3 show the lancing device 10 including a housing 20 generally comprising separable upper and lower housing half shells 22a, 22b, and a forward or proximal end 24 defining a lancet opening through which at least a sharp tip portion of a lancet projects at the extended position of its lancing stroke to penetrate the skin of a subject during the lancing process. As depicted, the housing 20 has a generally elongate ergonomic shape, wider at the back and tapering to a narrower front; however, alternate housing shapes can be utilized within the scope of the invention. The housing preferably has a lengthwise dimension in an axial direction between the proximal end 24 and a rear or distal end 26 which is greater than its side to side width in a transverse dimension, which in turn is greater than its thickness from top to bottom. The housing can be constructed of a substantially rigid durable material, for example plastic or composites.

A release button 30 projects through an opening 23 formed in the upper housing shell 22a to release engagement features of the lancet carrier when depressed, thereby actuating the device to propel the lancet along a lancet stroke from a charged or retracted position within the housing 20 (shown in FIG. 10) to an extended or lancing position (shown in FIG. 11) wherein at least the sharp tip portion of the lancet projects outwardly of the lancet opening at the proximal end of the housing 20. The lancet carrier then moves back to the neutral position (as will be described below) wherein engagement features of the lancet carrier re-engage catch features 33, 35 of arms 32, 34 generally extending transversely from the release button 30 (see FIG. 5). Preferably a resilient cantilevered finger 31 is coupled to the release button 30 for biasing the release button 30 within the opening 23 such that pressing the release button into the lancing device releases the engagement features of the lancet carrier from portions of the arms 32, 34 (see FIG. 5).

A charging mechanism 40 comprising a charging actuator or user actuated charging handle portion 41 (having ribbed surface features 41a, 41b) forming a portion of one end of the housing shells 22a, 22b retracts the lancet carrier and energizes the drive mechanism to provide a motive force to propel the lancet along the lancing stroke when the device is actuated. In example embodiments, the charging mechanism 40 movably mounts between the upper and lower housing shells 22a, 22b at one end, and the charging actuator 41 generally aligns with and fills a void or cut-out portion 27a, 27b at the distal end 26 of the housing between half-shells 22a, 22b to form a generally continuous outer contour of the lancing device 10. Preferably, the charging mechanism 40 comprises engagement features for movably mounting to alignment portions of the housing half-shells 22a, 22b. For example, the engagement features can be laterally offset rails 42a, 42b forming a portion of the charging mechanism 40 engage a portion of ribs 47a, 47b formed within the lower housing shell 22b for guidance and support when translationally retracting the charging actuator 41 of the charging mechanism 40 (see FIG. 5). As depicted, the charging actuator 41 can be a separate body from the housing 20 or the charging actuator can be an integral flexing or otherwise articulated part of the housing.

Optionally, the lancing device 10 can include an endcap or nose-cone portion 50. In example embodiments, the endcap 50 includes a cap base 52, a cap adjuster 54 and a cap cover 56 (see FIG. 3). Preferably, the elements of the endcap 50 include interengaging surface features for coupling to each other and/or coupling to the housing 20 near the proximal end 24 of the lancing device 10. Optionally, the endcap 50 can be adjustable to increase or decrease the depth of penetration of the lancet tip projecting external of the housing 20 (see FIGS. 8-9). In example embodiments, the cap cover 56 is adjustably secured to the cap base 52 for moving axially relative thereto so that the depth of penetration of the lancet projecting external of the housing 20 is determined by the position of the cap cover 56 relative to the cap base 52. According to one example form, the cap base 52 includes both a detent (unshown), configured for selectively engaging index indents 55 of the cap adjuster 54, and a detent 53 for contacting an arcuate flange extending from the cap adjuster 54, wherein rotation of the cap cover 56 moves the same forward or rearward relative to the cap base 52. Optionally, the cap cover 56 is provided with clear indication of the depth settings, for example, detents 57 formed along the periphery of the cap cover 56 and a detent 58 formed along the periphery of the cap base 52.

FIGS. 3-12 show the drive mechanism 70 of the lancing device 10 according to a first example embodiment of the present invention. Preferably, the lancing device and/or drive mechanisms of the present invention provide a plurality of benefits for minimizing the discomfort and/or pain a subject may feel or physiologically perceive when obtaining a sample of blood. In example embodiments, the drive mechanism utilizes one continuous motion to propel the lancet along the lancing stroke, advancing the lancet out (in a first axial direction) and retracting it back (in a second, opposite axial direction) relative to the housing of the lancing device to prick a user's skin, while reducing or eliminating impact between hard stop surfaces and the possibility for multiple punctures. The drive mechanism comprises a lancet carrier translationally mounted to a portion of the lancing device, a drive crank mechanism rotatably mounted to another portion of the lancing device, and a link pivotally coupled therebetween.

In general, the lancet carrier 80 is translationally mounted to slide within an axial bore or channel through a drive core or chassis 60. The link 90 includes a proximal or first end for coupling to a portion of the lancet carrier 80 and a distal or second end for coupling to a pivotal crank mechanism 100. The double-acting crank mechanism 100 generally includes a crank member 102 rotationally mounted relative to a portion of the crank mechanism 100, the eccentric pin or surface feature 104 mounted to, or through, the crank member 102 for coupling to the second end of the link 90, and two biasing members 120, 124 for constraining the circular rotation or a degree of rotation of the crank member 102. Preferably, the pivotal crank mechanism 100 provides one continuous, single-direction motion (clockwise or counter-clockwise) for propelling the lancet carrier in the first axial direction from a retracted position within the housing 20 to an extended or advanced position with the sharp tip portion of the lancet projecting out of the housing, and then moving in the second axial direction back to a neutral position. When the charging actuator 40 is retracted, a bar 51 mounted to the charging actuator contacts the eccentric pin 104 and pushes it rearwardly, therefore rotating the crank mechanism 100 and pulling the link 90 and the carrier 80 in the rearward direction. Alternatively, when the charging actuator 40 is retracted rearwardly, an arm 44 mounted to the charging actuator and generally extending transversely therefrom, axially retracts the lancet carrier and charges the drive mechanism of the lancing device 10.

Figure 4:
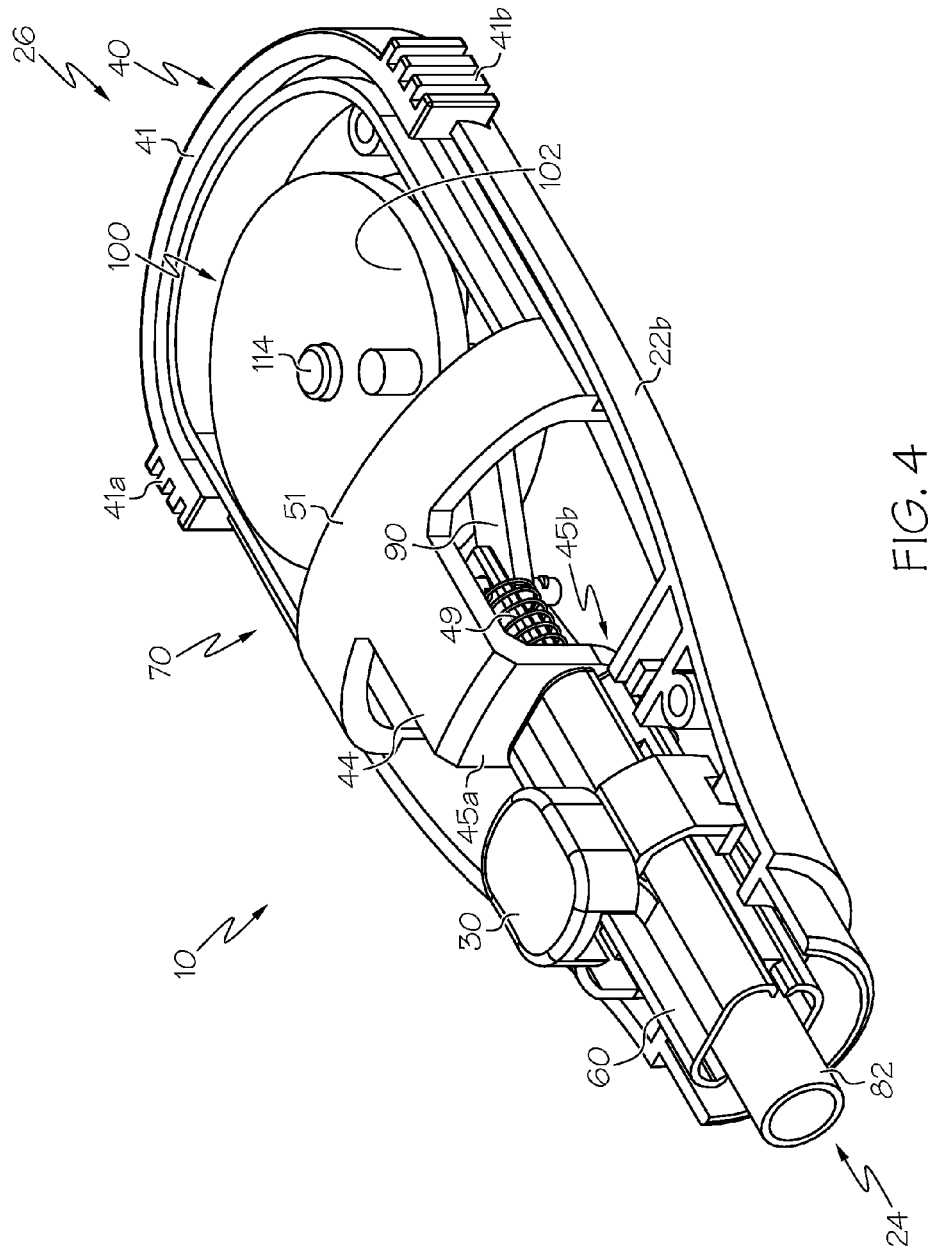
FIG. 4 shows the lancing device of FIG. 1 with portions of its external housing removed to show internal components thereof.
Figure 5:
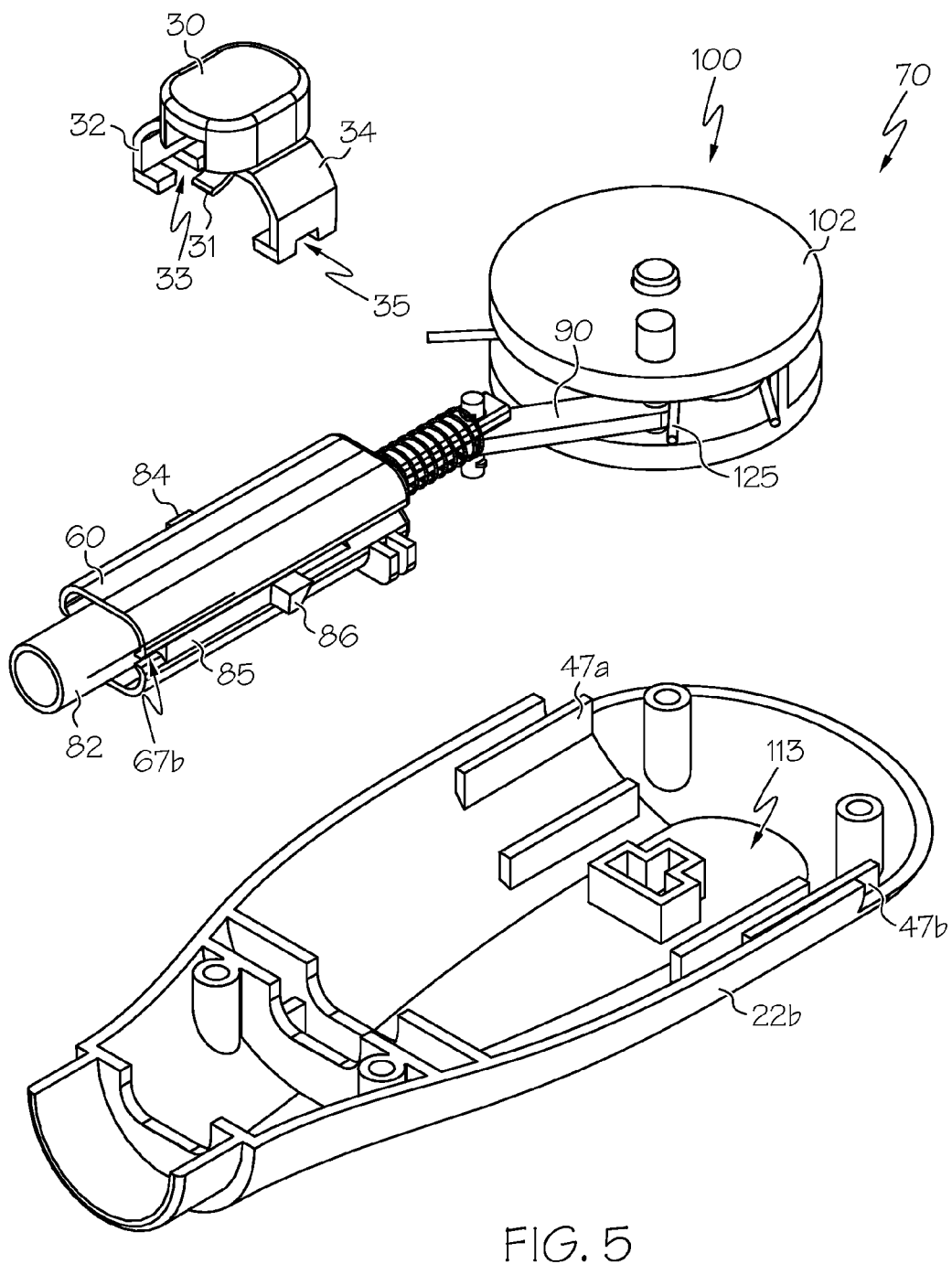
FIG. 5 is a partial assembly view of the lancing device of FIG. 1 with portions removed to show internal components thereof.

As depicted in FIGS. 4-5, the drive mechanism 70 is generally in the form of a slider-crank mechanism, whereby rotation of the crank mechanism 100 toggles the link 90 and drives the translationally mounted lancet carrier 80 axially along the lancing stroke. In example forms, the lancet carrier 80 is generally elongate and extends from a proximal end to a distal end. Preferably, the proximal end includes a collar or sleeve 82 for receiving a lancet and the distal end includes an opening or receiver 88 for receiving a hinge pin coupling 92 near a first end of the link 90. For engagement and selective disengagement with the release button 30, the lancet carrier 80 includes arms 83, 85 and catch tabs 84, 86 extending generally transverse to the long axis of the carrier 80 between the proximal and distal ends for movably mounting within elongated parallel side channels 67a, 67b of the chassis 60. Optionally, the catch tabs 84, 86 include inclined surface features configured to engage and release cooperating contact faces of the release button 30 upon engagement and disengagement thereof.

The chassis 60 is generally positioned near the proximal end 24 of the housing 20, extending from a distal end 61 to a proximal end 62 wherein engagement tabs or fingers 63b (and an un-shown opposing tab) engage within cooperating recesses of the housing. In example embodiments, the distal end 82 of the lancet carrier 80 extends through an opening (unshown) near the proximal end 62 of the chassis 60, and the proximal end of the lancet carrier extends through an orifice 45 that extends through the arm 44 of the charging mechanism 40 and an optional return or biasing spring 49. As depicted in FIG. 4, the arm 44 comprising the orifice 45 includes an anterior surface 45a for contact with a distal wall 62 of the chassis 60, and a posterior surface 45b for contact with a portion of the biasing spring 49. Preferably, the charging mechanism 40 is configured for retracting the lancet carrier 80 while allowing the same to move therethrough when driving the lancet along the lancing stroke.

Figure 7:
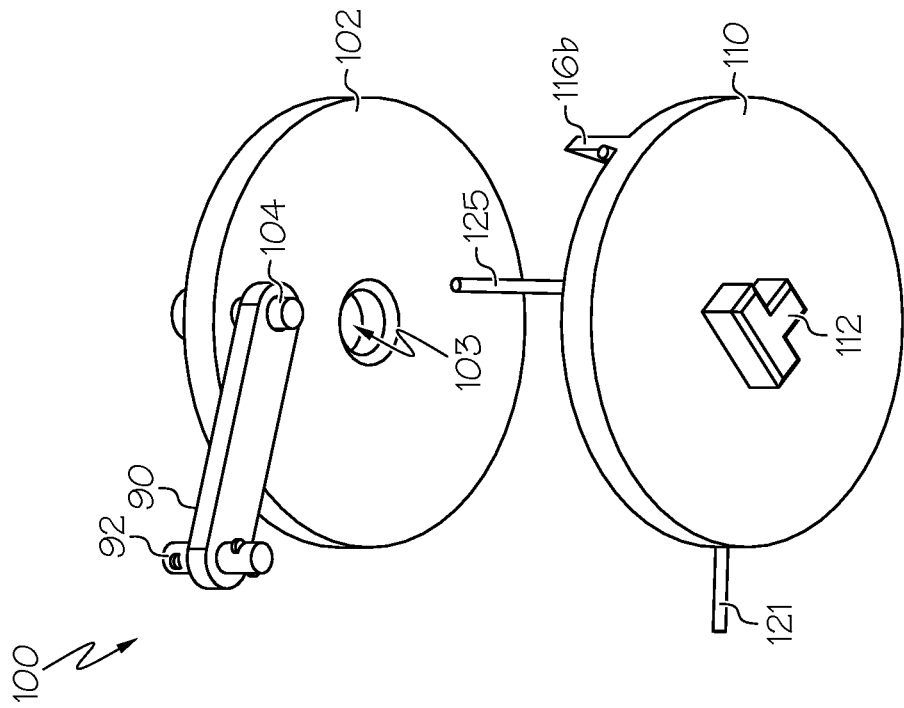
FIG. 7 is a partial assembly view showing a bottom perspective of the drive mechanism of the lancing device of FIG. 1.
Figure 6:
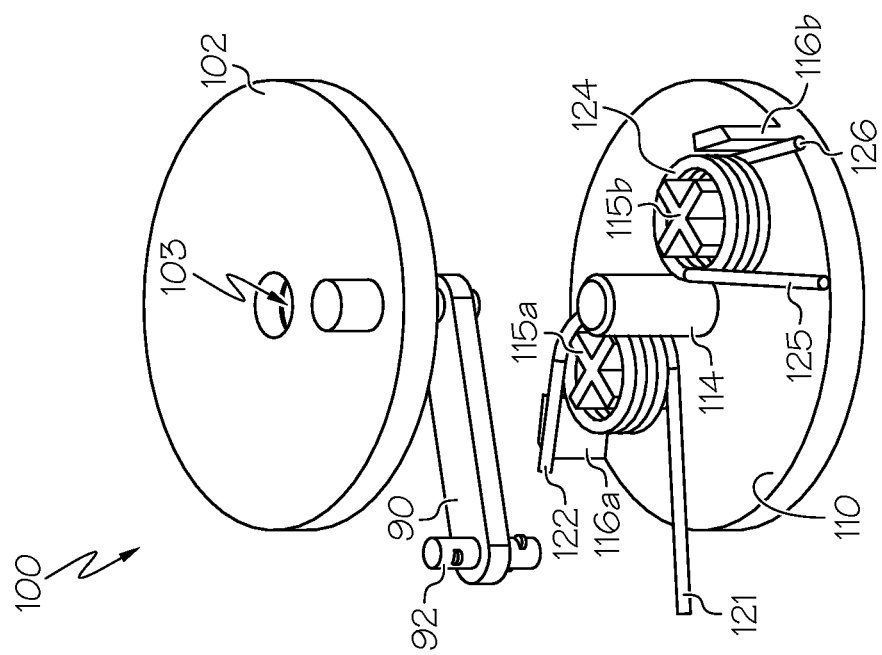
FIG. 6 is a partial assembly view showing a top perspective of the drive mechanism of the lancing device of FIG. 1.

FIGS. 6-7 show partial assembly views of the drive crank mechanism 100. In example forms, the pivotal drive mechanism 100 includes the crank member 102, a base member 110, and the two biasing members 120, 124. As depicted, the crank member 102 comprises a centrally positioned opening 103 for receiving and engaging a pivot post or axle 114 of the base member 110, thereby allowing the crank member 102 to rotate about an axis of rotation that is generally perpendicular to the path of travel of the lancet along its lancing stroke. The base member 110 includes a plurality of features for providing engagement with the housing 20, the crank member 102, and the two biasing members 120, 124. In one example form, the biasing members 120, 124 are torsion springs having first arms 121, 125 and second arms 122, 126 for engagement with restriction tabs 116a, 116b of the base member 110 and the eccentric pin 104 and/or link 90 coupled thereto, thereby constraining the rotation of the crank member 102 within a range of rotational motion between a first angularly offset position defined by contact with the first arm 121 of biasing member 120 and a second angularly offset position defined by contact with the first arm 125 of biasing member 124. In alternate embodiments, the biasing members can be in the form of compression springs, or some combination of the two, depending on the configuration.

For mounting the pivotal drive mechanism to the housing, the base member includes a surface feature 112 projecting therefrom for engagement with an cooperating engagement feature 113 of the bottom housing shell 22b (see FIG. 5), thereby maintaining the drive crank mechanism 100 in a fixed position within the housing. Alternatively, the base member 110 or portions thereof can movably mount within the housing 20 to provide adjustment to the depth of puncture. For example, since the biasing members 120, 124 do not directly act on the lancet carrier, the pivotal drive mechanism can be adjustably positioned within the housing 20 to provide depth adjustment of the sharp tip portion of the lancet projecting external the housing while the guidance component (chassis 60) is held stationary to provide consistent guidance for the lancet carrier 80 regardless of the desired depth setting.

FIGS. 8-12 show the sequential operation of the lancing device 10 throughout the charging and actuation portions of the lancing procedure. As depicted, portions of the lancing device have been removed and/or are partially transparent for purposes of understanding the operation of the drive mechanism 70. In example embodiments, the circular rotation of the crank member 102 is constrained to a particular degree of rotation or range of motion of at least about 45 degrees to about 180 degrees, for example about 60-90 degrees. Preferably, the engagement features of the base member 110 for receiving the biasing springs 120, 124 are positioned such that the axial direction or path of travel of the lancet defines an axis of symmetry therebetween, thereby allowing the crank member 102 to drive the lancet along the lancing stroke by rotation in both a clockwise and a counter-clockwise direction. Throughout the sequential operation in both clockwise and counter-clockwise directions, the crank mechanism drives the lancet carrier 80 along the lancing stroke, generally moving the link 90 coupled therebetween between four angular positions (a first neutral position, a first charged position, a second neutral position, and a second charged position).

Figure 8:
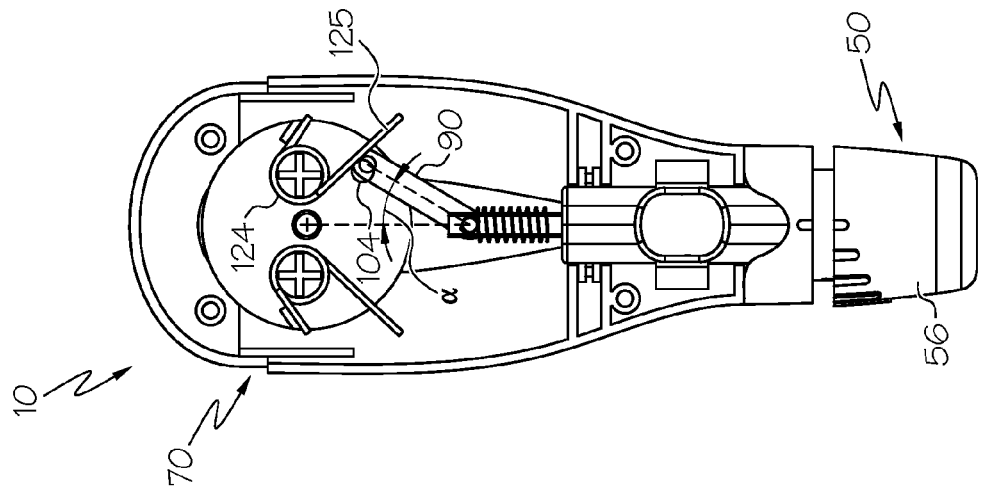
FIGS. 8-12 are top views of the lancing device of FIG. 1 with portions of its external housing removed, showing a sequence of operation thereof.
Figure 9:
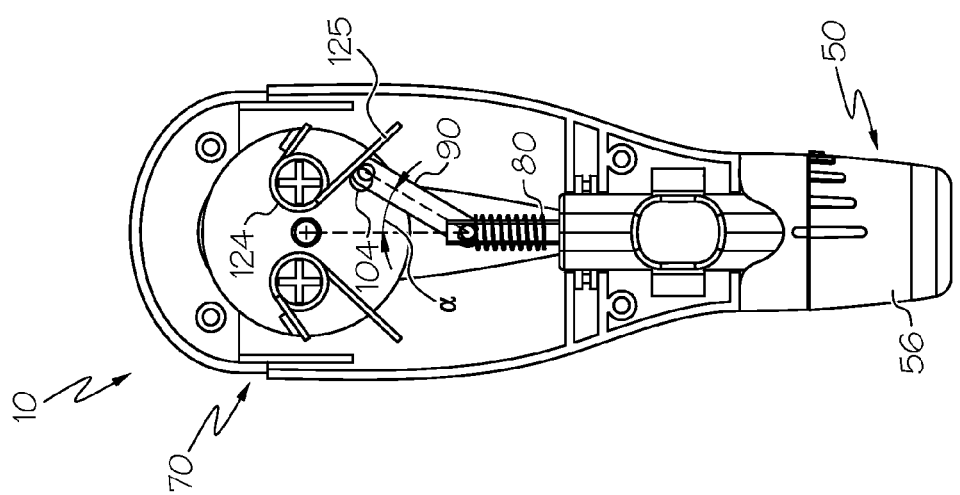
Figure 11:
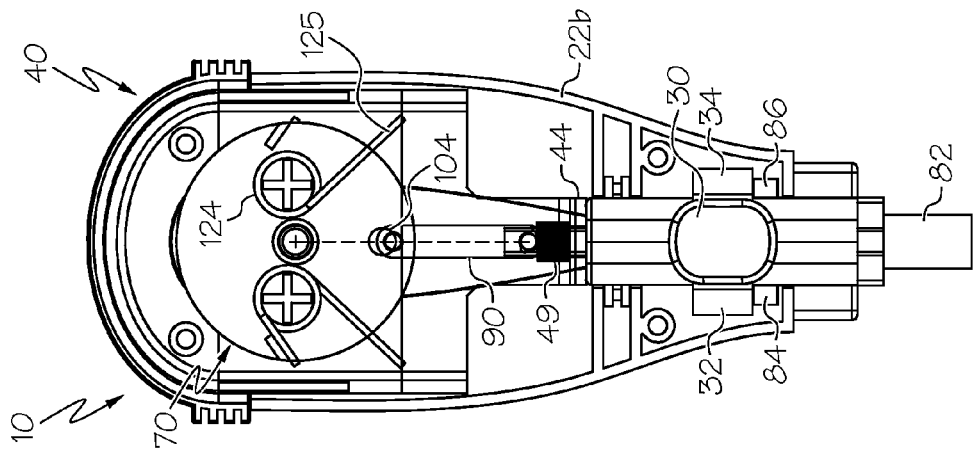

As depicted in FIGS. 8-9, the link 90 is in a first neutral position wherein the eccentric pin 104 coupled to the link 90 contacts the first arm 125 of the biasing member 124, resulting in the lancet carrier 80 indirectly mounted thereto being positioned in the neutral position. Preferably, the angle α of the link 90 relative to the axis of translation of the lancet carrier (indicated as the "axial" direction) is at least about 5 degrees to about 45 degrees, for example about 25-30 degrees. Additionally, the endcap 50 is adjustable between a first position corresponding to a maximum depth of puncture (see FIG. 8) and a second position corresponding to a minimum depth of puncture (see FIG. 9).

Figure 10:
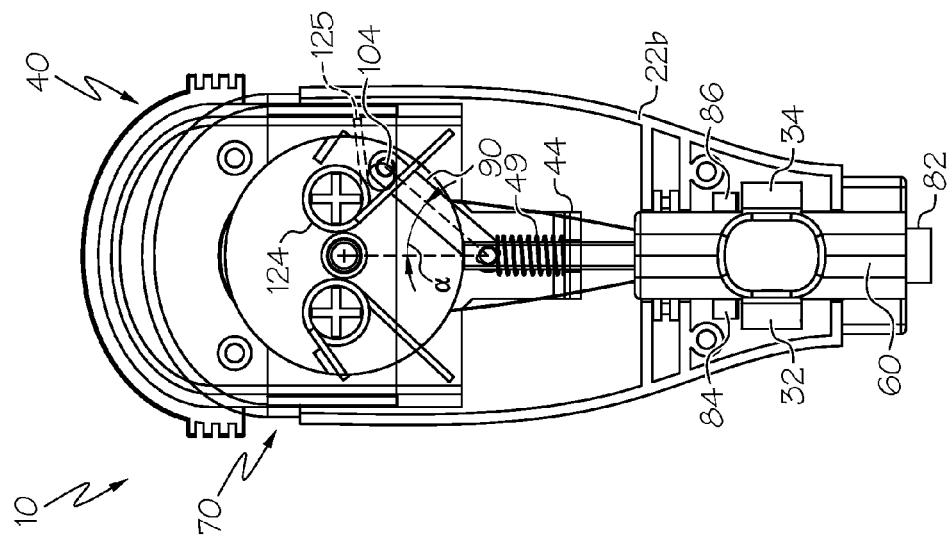

FIG. 10 shows the link 90 in a first charged position. In example embodiments, the charging mechanism 40 is retracted rearwardly, retracting the lancet carrier 80 within the housing to further charge the drive mechanism 70. Preferably, as the lancet carrier is retracted, the catch tabs 84, 86 move beyond the catch features 33, 35 of the arms 32, 34 of the release button 30, allowing the resilient cantilevered finger 31 to bias the release button 30 such that the catch features 33, 35 contact distal portions of the arms 32, 34 and prohibit further distal movement of the lancet carrier 80. As the lancet carrier 80 is retracted, the link 90 forces rotation (e.g., counter-clockwise) of the crank member 102 to charge or energize the first arm 125 of the biasing member 124, thereby positioning the link 90 in the first charged position. After charging is complete, the biasing member 49 moves the charging mechanism 40 back to a neutral position wherein the anterior surface 45a of the arm 44 contacts the proximal wall 64 of the chassis 60. Preferably, in the first charged position, the angle α of the link 90 relative to the axial direction is about 35-45 degrees, for example about 40 degrees. Additionally, to ensure a majority of the stored energy within the energized biasing member 124 acts on the link 90 in the desired direction, the angle α of the link in the first charged position is generally less than or equal to about 45 degrees.

Figure 12:
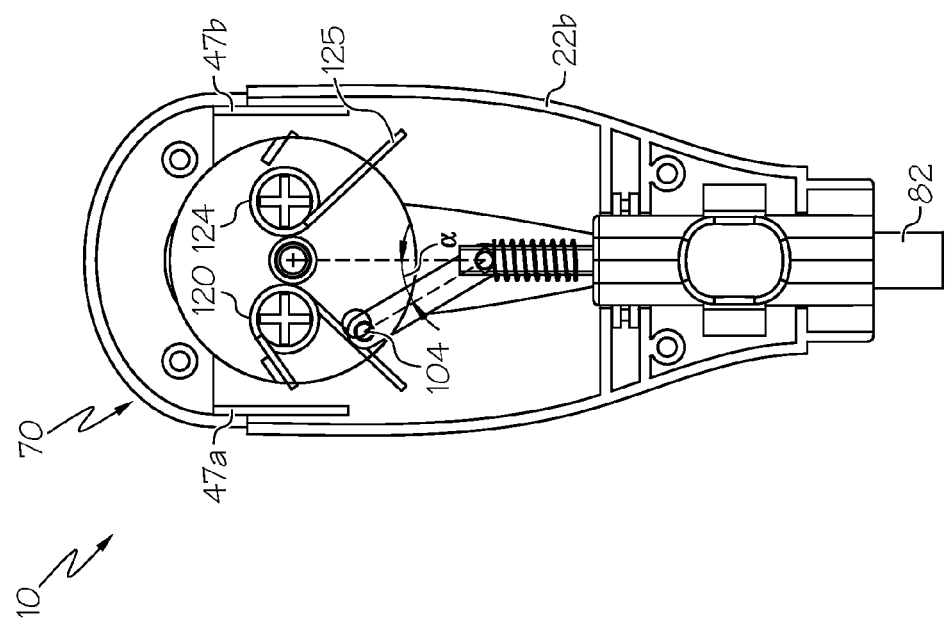

Upon actuating the release button 30 to disengage the catch tabs 84, 86 from the arms 32, 34, the first arm 125 of the biasing member 124 drives a continuous rotation of the crank member 102 in a first rotational direction (e.g., clockwise in FIGS. 8-12) to propel the lancet carrier 80 along both the advancing and retraction portions of the lancing stroke, moving the lancet carrier from a charged position within the housing 20 (FIG. 10), to an advanced position wherein at least the sharp tip portion of the lancet projects external of the housing to penetrate the subject's skin at a lancing site (FIG. 11), and back to a neutral position wherein the eccentric pin 104 contacts the first arm 121 of the biasing member 120 and positions the crank member at a second neutral position (FIG. 12). Preferably, as depicted in FIG. 12, the angle α of the link 90 in the second neutral position relative to the axial direction is substantially symmetric and similar to the angle α as described in FIGS. 8-9.

To charge the device again, the charging mechanism 40 is retracted and the link 90 forces rotation (e.g., clockwise) of the crank member 102 to energize the first arm 121 of the biasing member 120, thereby positioning the link 90 in a second charged position wherein the angle α of the link 90 relative to the axial direction is substantially symmetric and similar to the angle α as described in FIG. 10. Upon actuation of the release button 30, the first arm 121 of the biasing member 120 forces rotation (e.g., counter-clockwise) of the crank member 102 to propel the lancet carrier 80 along the advancing and retraction portion of the lancing stroke, further returning the crank member 102 to the first neutral position.

Throughout its use, the biasing members 120, 124 of the drive crank mechanism 100 alternate between driving the crank member for propelling the lancet carrier and constraining further rotation of the crank member 102. For example, when moving from the first charged position to the second neutral position, the biasing member 124 functions to drive the crank member 102 and the biasing member 120 functions to constrain or limit further rotation of the crank member. Alternatively, when moving from the second charged position to the first neutral position, the biasing member 120 functions to drive the crank member 102 and the biasing member 124 functions to constrain or limit further rotation of the crank member. Because of the resilience of the biasing members, the sensation of vibration or impact is eliminated or substantially reduced relative to lancing devices wherein contact with a hard stop surface limits the lancing stroke.

Figure 13:
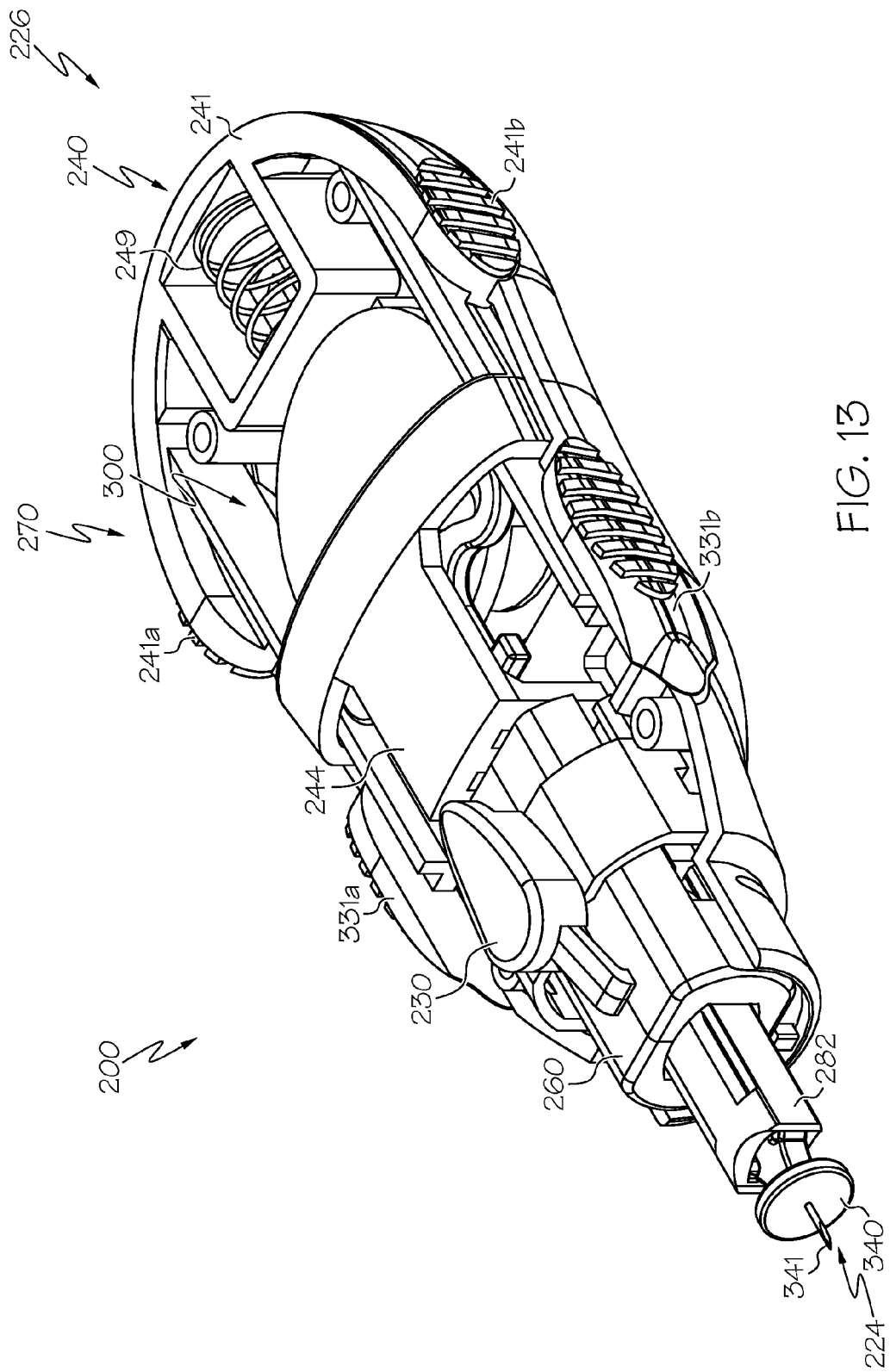
FIG. 13 is a perspective view of a lancing device according to another example embodiment of the present invention, with portions of its external housing removed to show internal components thereof.
Figure 14:
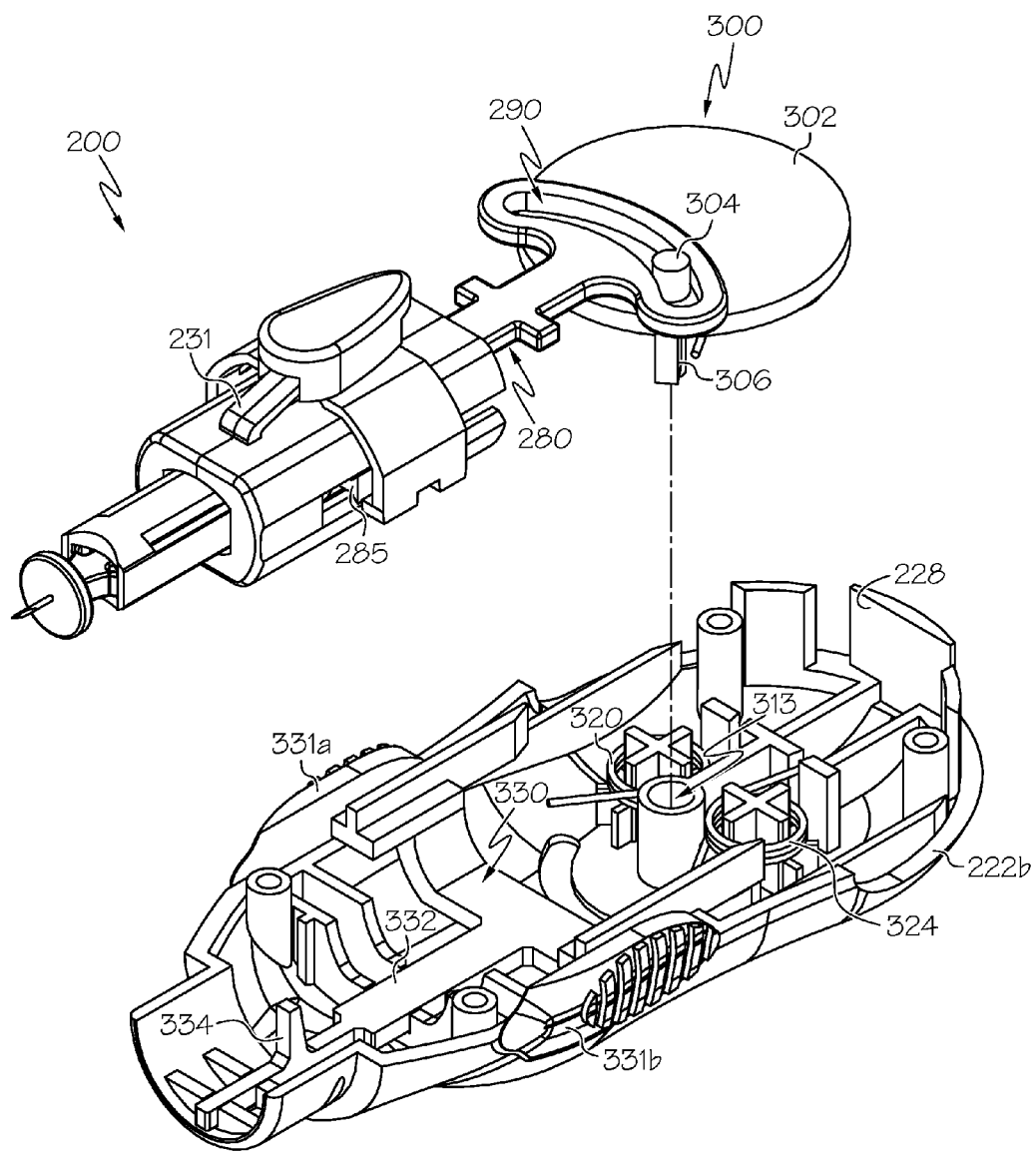
FIG. 14 is a partial assembly view of the lancing device of FIG. 13 with portions removed to show internal components thereof.

FIGS. 13-14 show a lancing device 200 having a drive mechanism 270 according to another example embodiment of the present invention. The lancing device 200 is substantially similar to the lancing device 10 as described above, wherein one continuous rotational movement (clockwise or counter-clockwise) of a crank member 302 in a first or second direction, between a first angular position and a second angular position, drives a lancet 340 along an axial translational out and back lancing stroke, having an advancing stroke portion in a first axial direction and a retraction stroke portion in an opposite second axial direction, to prick a subject's skin with a sharp tip portion 341 of the lancet.

In example forms, the drive mechanism 270 includes a lancet carrier 280 and a drive-crank mechanism 300. The lancet carrier comprises a cam path 290 formed by a slot or groove near the distal end of the lancet carrier, within which an eccentric pin 304 of a crank member 302 is slidably engaged, thereby allowing rotation (clockwise or counter-clockwise) of the crank member 302 to drive the lancet carrier from a retracted position to an advanced position (in the first axial direction), and back to a neutral position (in the second axial direction). Preferably, the crank member 302 includes a post 306 axially aligned with the eccentric pin 304 for engaging biasing members 320, 324 to propel the lancet along the lancing stroke, and optionally also to limit the angular extent of rotation of the crank 302 in each direction. Alternatively, the ends of the cam path 290 define the limits of rotation of the crank 302. In the depicted embodiment, the cam path 290 defines an arcuate curvature that is generally inverse to the curve formed by the outer circumference of the crank member 302. The cam path 290 lies in a plane generally parallel to the plane of the crank member 302, and at least partially overlies the crank member.

Optionally, a charging mechanism 240 includes a receiver for retaining a biasing spring 249 near the proximal end 226 of the lancing device 200 for returning the charging handle 241 to its retracted state after actuating the charging handle to energize the device. Additionally, the lancing device 200 may include an ejection mechanism 330 for selectively engaging and ejecting the lancet 340. The ejection mechanism 330 generally includes user-actuated grips 331a, 331b, an elongate member 332 extending towards the proximal end 224, and an engagement finger 334 extending transversely therefrom to push a lancet out of engagement with the receiver of the lancet carrier.

Figure 15:
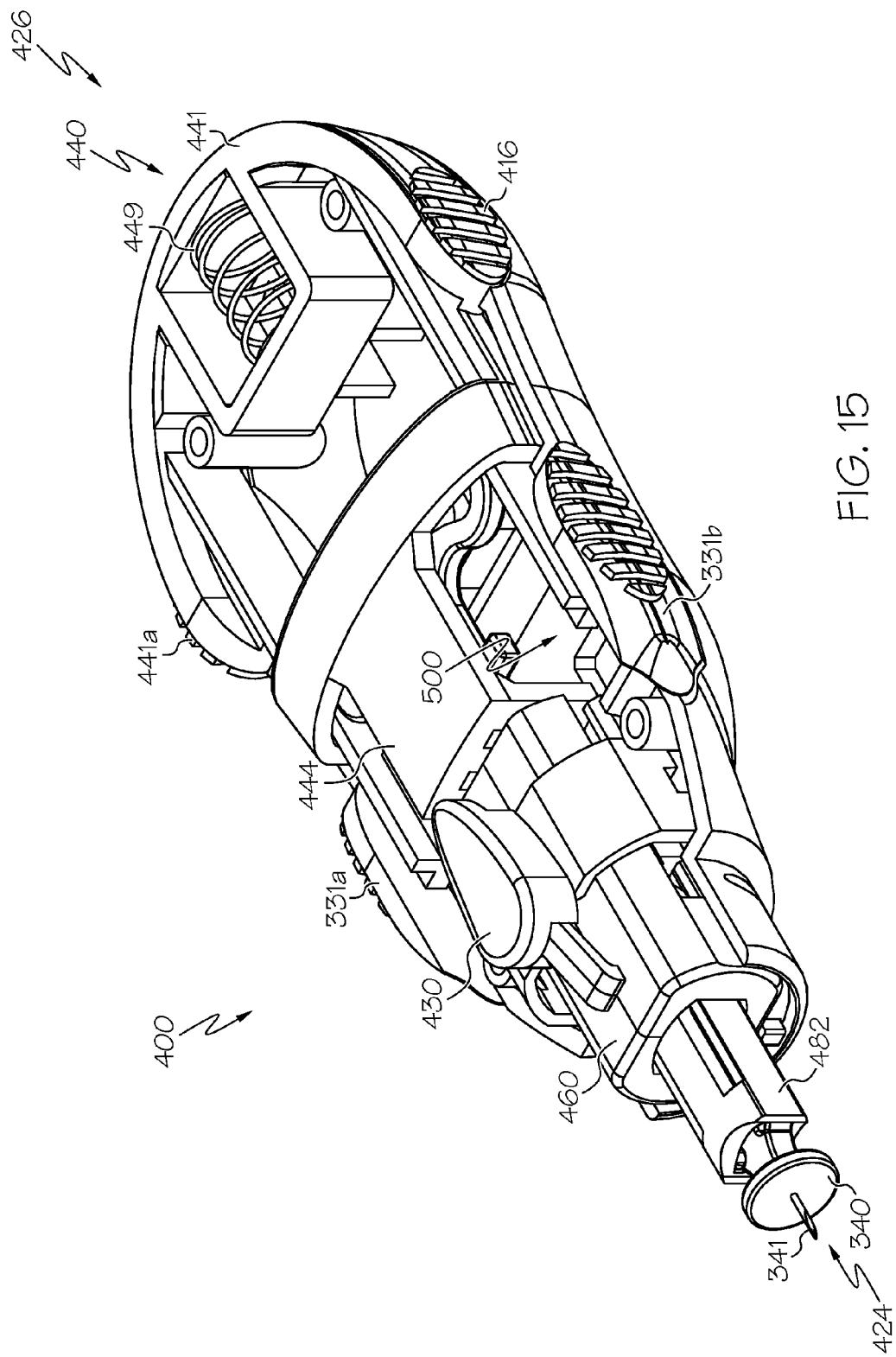
FIG. 15 is a perspective view of a lancing device according to another example embodiment of the present invention, with portions of its external housing removed to show internal components thereof.
Figure 16:
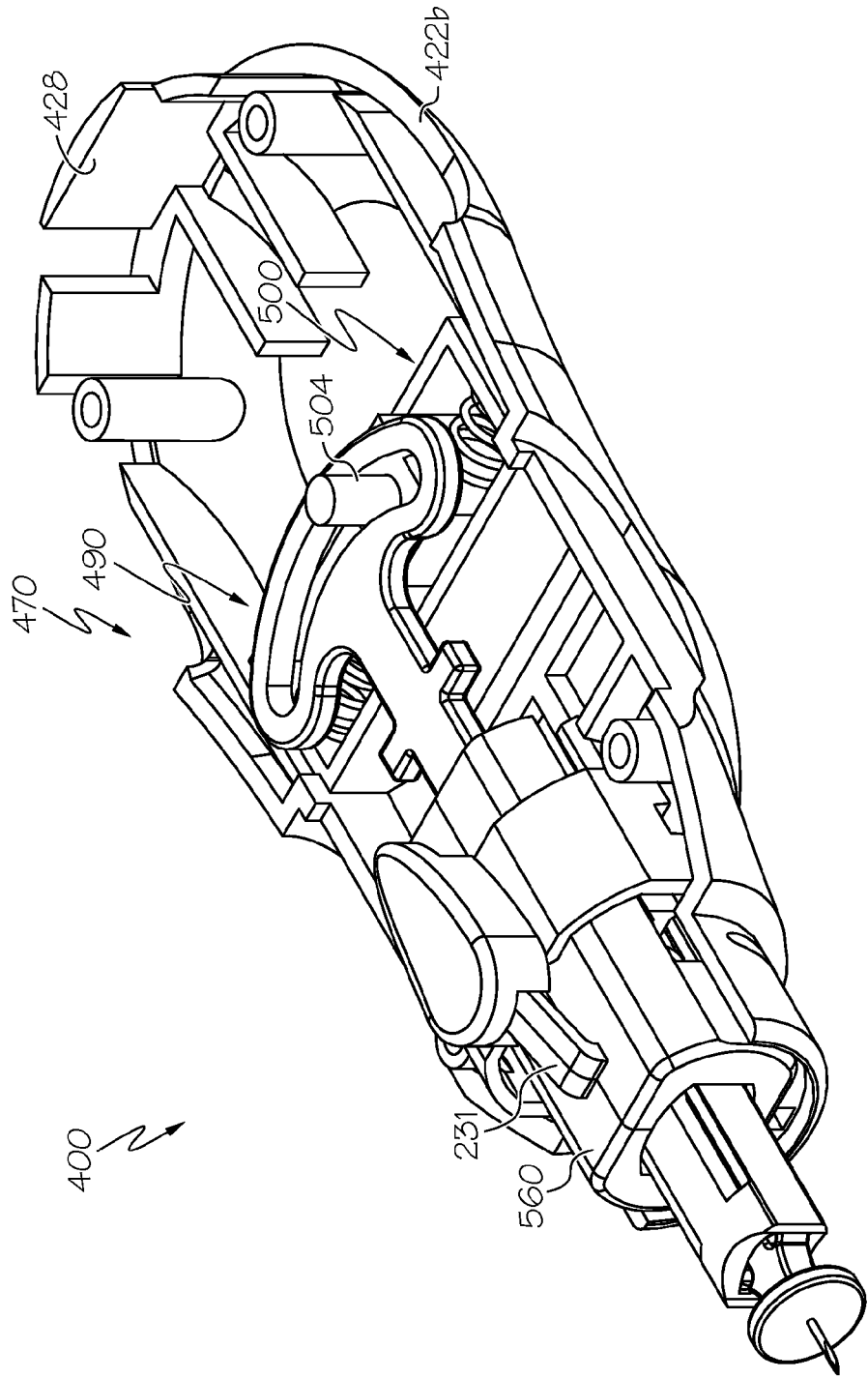
FIG. 16 is a perspective view of the lancing device of FIG. 15 with portions removed to show internal components thereof.
Figure 17:
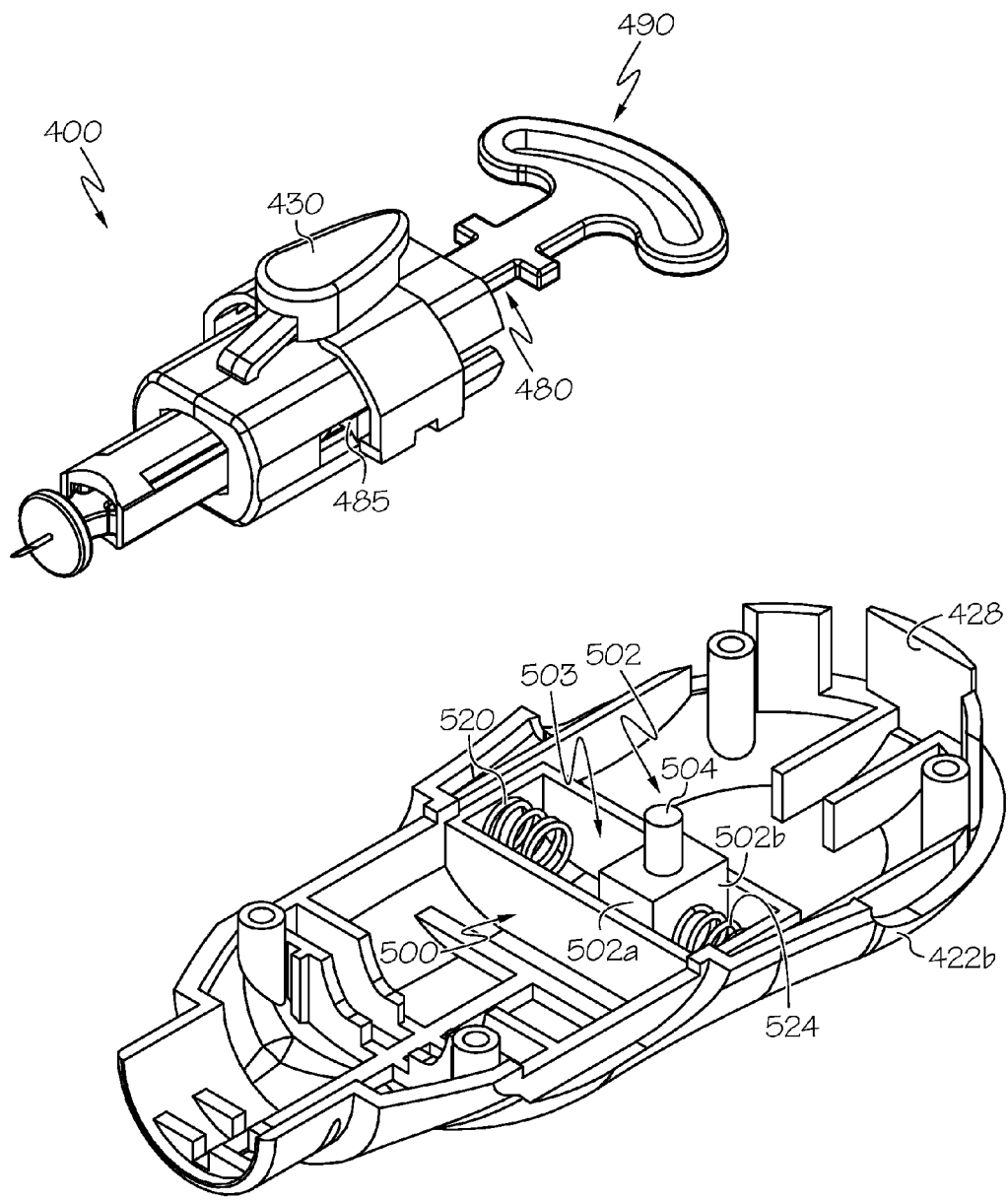
FIG. 17 is a partial assembly view of the lancing device of FIG. 15 with portions removed to show internal components thereof.

FIGS. 15-17 show a lancing device 400 having a drive mechanism 470 according to yet another example embodiment of the present invention. The lancing device 400 is substantially similar to the lancing device 200 as described above, and comprises a lancet carrier 480 having a cam path 490 substantially similar to the cam path 290 of the above-described embodiment. The drive mechanism 470 includes a lancet carrier 480 and a shuttle mechanism 500.

The shuttle mechanism 500 generally includes a shuttle member 502 mounted within a channel or slot 503 defined in the housing 422b. First and second biasing members 520, 524 are mounted at each end of the slot 503 to propel the shuttle member 502 back and forth, and optionally also to limit the extent of travel of the shuttle member. The shuttle member 502 comprises an engagement pin 504 extending therefrom and contact features or side surfaces 502a, 502b, 502c, 502d for engaging portions of the slot 503 and the biasing members 520, 524.

The shuttle 502 is translationally driven back and forth along a transverse path, generally perpendicular to the axial direction of travel of the lancet. A single continuous motion of the shuttle member 502 in either a first transverse direction or a second transverse direction cause the pin 504 to traverse the cam path 490, and thereby drives the lancet 340 through its lancing stroke, out (in a first or advancing axial direction) and back (in a second or retracting axial direction), to prick a subject's skin with the sharp tip portion 341 of the lancet and return the lancet to a neutral position within the housing.

While the invention has been described with reference to preferred and example embodiments, it will be understood by those skilled in the art that a variety of modifications, additions and deletions are within the scope of the invention, as defined by the following claims.

What is claimed is:

1. A lancing device drive mechanism for driving a lancet along a lancing stroke, the drive mechanism comprising:
   a base member comprising an axle and first and second restriction tabs;
   a crank member mounted to the axle of the base member and rotational about an axis of rotation within a range of rotatable movement, the crank member comprising an eccentric pin;
   a lancet carrier for carrying the lancet along a translational path of travel defining the lancing stroke of the lancet;
   a link having a first end pivotally connected to the eccentric pin of the crank member and a second end pivotally connected to the lancet carrier, the link coupling rotation of the crank member to drive translation of the lancet carrier; and
   an opposed pair of springs, a first spring of the opposed pair having a first end abutting against the first restriction tab of the base member and a second end contacting the eccentric pin of the crank member to drive the crank member in a first direction, and a second spring of the opposed pair having a first end abutting against the second restriction tab of the base member and a second end contacting the eccentric pin of the crank member to drive the crank member in a second direction opposite the first direction.

2. The drive mechanism of claim 1, wherein the opposed pair of springs comprise a pair of torsion springs, each torsion spring comprising an inner arm and an outer arm.

3. The drive mechanism of claim 1, wherein the base member is fixed with respect to the axis of translation of the lancet carrier.

4. The drive mechanism of claim 3, wherein the range of rotatable movement of the crank member is between 45 degrees and 180 degrees with respect to the base member.

5. The drive mechanism of claim 1, wherein a continuous rotation of the crank member through the range of rotatable movement moves the lancet carrier through a complete lancing stroke.

6. A method of propelling a translating lancet carrier along a lancing stroke, the method comprising applying a unidirectional force to the lancet carrier through a drive mechanism, wherein the drive mechanism comprises a rotational crank member defining a range of rotational movement, a base member having a first restriction tab and a second restriction tab, and a link having a first end pivotally connected to the crank member and a second end pivotally connected to the lancet carrier; wherein the link traverses a range of pivotal movement between 5 degrees and 45 degrees with respect to an axis of translation of the lancet carrier, wherein the method further comprises imparting pivotal movement to the link by actuation of a pair of opposed springs situated between the crank member and the base member, the pair of opposed springs comprising a first spring and a second spring, the first spring having a first portion directly engaging the first restriction tab and a second portion constraining motion of the crank member at a first end of its range of rotational movement, and the second spring having a first portion directly engaging the second restriction tab and a second portion constraining motion of the crank member at a second end of its range of rotational movement.

7. The method of claim 6, further comprising completing the lancing stroke through a single continuous rotation of the rotational crank member across the range of rotational movement.

* * * * *